United States Patent [19]
Grote et al.

[11] Patent Number: 6,046,353
[45] Date of Patent: Apr. 4, 2000

[54] METHOD OF MAKING (S)-3-(AMINOMETHYL)-5-METHYLHEXANOIC ACID

[75] Inventors: Todd Michel Grote; Brian Keith Huckabee, both of Holland; Thomas Mulhern, Hudsonville; Denis Martin Sobieray, Holland, all of Mich.; Robert Daniel Titus, Indianapolis, Ind.

[73] Assignee: Warner-Lambert Company, Morris Plains, N.J.

[21] Appl. No.: 09/140,163

[22] Filed: Aug. 26, 1998

Related U.S. Application Data

[62] Division of application No. 08/796,159, Feb. 6, 1997, Pat. No. 5,840,956, which is a division of application No. 08/671,881, Jun. 28, 1996, abandoned, which is a division of application No. 08/474,874, Jun. 7, 1995, Pat. No. 5,637,767.

[51] Int. Cl.⁷ .................................................. C07C 255/00
[52] U.S. Cl. ......................... 558/442; 558/398; 558/399; 558/430; 558/432; 558/433; 558/434
[58] Field of Search ..................... 558/442, 398, 558/399, 430, 432, 433, 434

[56] References Cited

U.S. PATENT DOCUMENTS

| | | | |
|---|---|---|---|
| 2,516,307 | 7/1950 | Floyd | 260/31.8 |
| 3,110,723 | 11/1963 | De Benneville et al. | 260/465.4 |
| 3,133,954 | 5/1964 | De Benneville et al. | 260/465.4 |
| 3,444,161 | 5/1969 | Nagata | 260/239.55 |
| 3,654,339 | 4/1972 | Aus der Funten et al. | 260/464 |
| 4,290,972 | 9/1981 | Yoneta et al. | 260/465 B |
| 4,428,887 | 1/1984 | Tou | 260/465 |
| 4,760,089 | 7/1988 | Chambers et al. | 514/523 |
| 5,132,451 | 7/1992 | Jennings et al. | 562/507 |
| 5,366,987 | 11/1994 | Lee et al. | 514/378 |
| 5,563,175 | 10/1996 | Silverman et al. | 514/561 |

FOREIGN PATENT DOCUMENTS

| | | |
|---|---|---|
| 0100019A1 | 2/1984 | European Pat. Off. . |
| 0450577A1 | 10/1991 | European Pat. Off. . |
| 125777 | 4/1985 | Poland . |
| 93/23383 | 11/1993 | WIPO . |

OTHER PUBLICATIONS

Elderfield, R. C., et al., "Further Syntheses of Primaquine Analogs," *American Chem. Society*, Sep., 20, 1955, vol. 77, pp. 4819–4822.

PCT International Search Report.

Lange, J., et al., "Direct Pyridazine Ring Synthesis from β-cyano Esters. A Facile Synthesis of the Derivatives of Tetrahydro-3, 6-Pyridazinedione 3-Hydrazone," *Synthetic Communications*, 1993, vol. 23, No. 10, pp. 1371–1377.

Andruszkiewicz, R., and Silverman, R. B., "A Convenient Synthesis of 3-Alkyl-4-aminobutanoic Acids," *Journal of Synthetic Organic Chemistry*, Dec., 1989, No. 12, pp. 953–955.

Jung, M. J., et al., "Mechanism of the Stereospecific Irreversible Inhibition of Bacterial Glutamic Acid Decarboxylase by (R)–(—)–4–Aminohex–5–ynoic Acid, An Analogue of 4–Aminobutyric Acid," *Biochemistry*, 1978, vol. 17, No. 13, pp. 2628–2632.

Carruthers, N. I., et al., "Synthesis and Resolution of β–(Aminomethyl)–4–Chlorobenzeneethanesulfinic Acid. A Potent Gaba$_B$ Receptor Ligand," *Bioorganic & Medicinal Chemistry Letters*, 1995, vol. 5, No. 3, pp. 237–240.

*Primary Examiner*—Michael L. Shippen
*Attorney, Agent, or Firm*—Linda A. Vag

[57] ABSTRACT

A method of making (±)-3-(aminomethyl)-5-methylhexanoic acid that comprises condensing isovaleraldehyde with

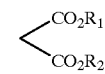

to form primarily

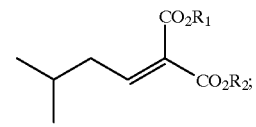

reacting the

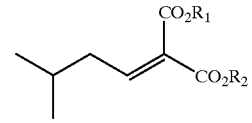

with a cyanide source to form

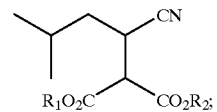

decarboxylating the

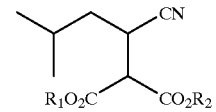

to form

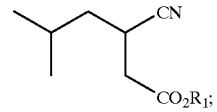

hydrolyzing the

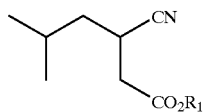

with an alkali or alkaline earth metal hydroxide to form an alkali or alkaline earth metal carboxylate salt; and hydrogenating the alkali or alkaline earth metal carboxylate salt to form (±)-3-(aminomethyl)-5-methylhexanoic acid, wherein $R_1$ and $R_2$ are the same or different and are hydrogen, $C_1$–$C_6$ alkyl, aryl, benzyl, or $C_3$–$C_6$ cycloalkyl. The present invention also provides a method of making (±)-3-(aminomethyl)-5-methylhexanoic acid that comprises condensing isovaleraldehyde with

to form primarily

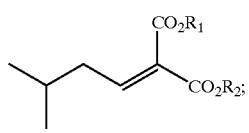

reacting the

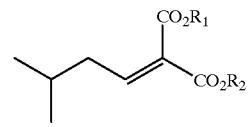

with a cyanide source to form

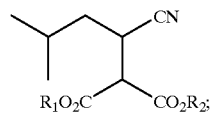

decarboxylating the

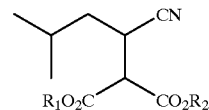

to form an alkali or alkaline earth metal carboxylate salt; and hydrogenating the alkali or alkaline earth metal carboxylate salt to form (±)-3-(aminomethyl)-5-methylhexanoic acid.

2 Claims, No Drawings

METHOD OF MAKING (S)-3-(AMINOMETHYL)-5-METHYLHEXANOIC ACID

CROSS-REFERENCE TO RELATED APPLICATIONS

This application is a divisional of U.S. application Ser. No. 08/796,159 filed Feb. 6, 1997, now U.S. Pat. No. 5,840,956, which is a divisional of U.S. application Ser. No. 08/671,881 filed Jun. 28, 1996, now abandoned, which is a divisional of U.S. application Ser. No. 08/474,874 filed Jun. 7, 1995, now U.S. Pat. No. 5,637,767.

FIELD OF THE INVENTION

This invention relates to a method of making (±)-3-(aminomethyl)-5-methylhexanoic acid and to a method of obtaining (S)-3-(aminomethyl)-5-methylhexanoic acid from (±)-3-(aminomethyl)-5-methylhexanoic acid.

BACKGROUND OF THE INVENTION 3-(Aminomethyl)-5-methylhexanoic acid, which is also called β-isobutyl-γ-aminobutyric acid or isobutyl-GABA, is a potent anticonvulsant. Isobutyl-GABA is related to the endogenous inhibitory neurotransmitter γ-aminobutyric acid or GABA, which is involved in the regulation of brain neuronal activity.

It is thought that convulsions can be controlled by controlling the metabolism of the neurotransmitter γ-aminobutyric acid. When the concentration of GABA diminishes below a threshold level in the brain, convulsions result (Karlsson A., et al., *Biochem. Pharmacol.*, 1974;23:3053–3061), and when the GABA level rises in the brain during convulsions, the seizures terminate (Hayashi T., *Physiol.* (London), 1959;145:570–578). The term "seizure" means excessive unsynchronized neuronal activity that disrupts normal function.

Because of the importance of GABA as an inhibitory neurotransmitter, and its effect on convulsive states and other motor dysfunctions, a variety of approaches have been taken to increase the concentration of GABA in the brain. In one approach, compounds that activate L-glutamic acid decarboxylase (GAD) have been used to increase concentrations of GABA, as the concentrations of GAD and GABA vary in parallel and increased GAD concentrations result in increased GABA concentrations (Janssens de Varebeke P., et al., *Biochem. Pharmacol.*, 1983;32:2751–2755; Loscher W., *Biochem. Pharmacol.*, 1982;31:837–842; Phillips N., et al., *Biochem. Pharmacol.*, 1982;31:2257–2261). For example, the compound (±)-3-(aminomethyl)-5-methylhexanoic acid, a GAD activator, has the ability to suppress seizures while avoiding the undesirable side effect of ataxia.

It has been discovered that the anticonvulsant effect of isobutyl-GABA is stereoselective. That is, the S-stereoisomer of isobutyl-GABA shows better anticonvulsant activity than the R-stereoisomer. See, for example, Yuen, et al., in *Bioorganic & Medicinal Chemistry Letters*, 1994;4(6):823–826. Thus, it would be beneficial to have an efficient process for the synthesis of the S-stereoisomer of isobutyl-GABA.

Presently, (S)-3-(aminomethyl)-5-methylhexanoic acid has been prepared by two synthetic routes. These routes each use reactions that require n-butyllithium, and both routes contain a step that must be carried out at low temperatures ($\leq -35°$ C.) under carefully controlled conditions. These synthetic routes include the use of (4R,5S)-4-methyl-5-phenyl-2-oxazolidinone as a chiral auxiliary to introduce the stereochemical configuration needed in the final product. See, for example, U.S. Ser. No. 08/064,285, which is hereby incorporated by reference. Although these routes provide the target compound in high enantiomeric purity, they are difficult to conduct on large-scale and use expensive reagents which are difficult to handle.

In addition, (±)-isobutyl GABA can be synthesized in accordance with Andruszkiewicz, et al., *Synthesis*, 1989;953. The synthesis described therein uses potentially unstable nitro compounds, including nitromethane, and an intermediate containing a nitro functional group, which is reduced to an amine in a potentially exothermic and hazardous reaction. The synthesis also uses lithium bis (trimethylsilylamide) at $-78°$ C. The present method does not use nitro compounds, require low temperatures, or require strongly basic conditions.

The present invention provides an efficient synthesis of isobutyl-GABA and provides for the resolution of racemic isobutyl-GABA to obtain the S-stereoisomer of isobutyl-GABA that avoids the above-identified problems.

SUMMARY OF THE INVENTION

The present invention provides the compounds

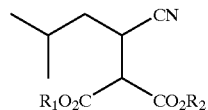

where $R_1$ and $R_2$ are the same or different and are hydrogen, $C_1$–$C_6$ alkyl, aryl, benzyl or $C_3$–$C_6$ cycloalkyl;

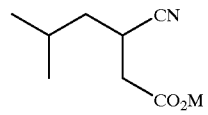

where M is hydrogen, an alkali metal, or an alkaline earth metal;

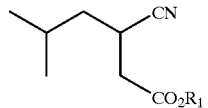

where $R_1$ is defined above; and

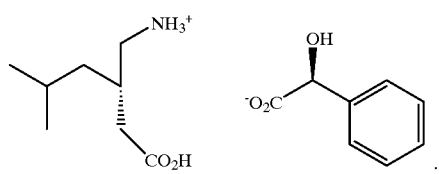

The present invention provides a method of making (±)-3-(aminomethyl)-5-methylhexanoic acid which comprises condensing isovaleraldehyde with

to form primarily

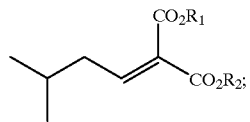

reacting the

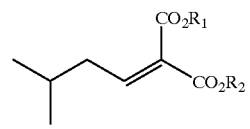

with a cyanide source to form

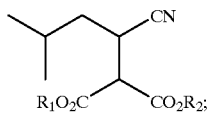

decarboxylating the

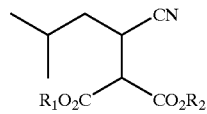

to form

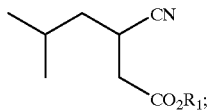

hydrolyzing the

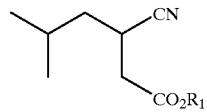

with an alkali or alkaline earth metal hydroxide to form an alkali or alkaline earth metal carboxylate salt; and hydrogenating the alkali or alkaline earth metal carboxylate salt to form (±)-3-(aminomethyl)-5-methylhexanoic acid, wherein $R_1$ and $R_2$ are the same or different and are hydrogen, $C_1$–$C_6$ alkyl, aryl, benzyl, or $C_3$–$C_6$ cycloalkyl.

A preferred method of making (±)-3-(aminomethyl)-5-methylhexanoic acid comprises condensing isovaleraldehyde with

to form primarily

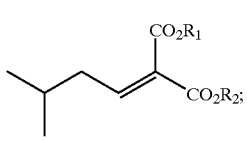

reacting the

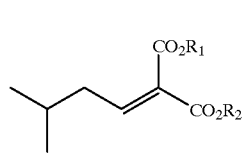

with a cyanide source to form

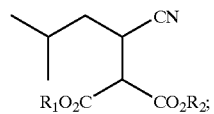

decarboxylating the

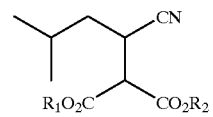

to form an alkali or alkaline earth metal carboxylate salt; and hydrogenating the alkali or alkaline earth metal carboxylate salt to form (±)-3-(aminomethyl)-5-methylhexanoic acid.

The present invention also provides a method for obtaining (S)-3-(aminomethyl)-5-methylhexanoic acid from (±)-3-(aminomethyl)-5-methylhexanoic acid which comprises combining (±)-3-(aminomethyl)-5-methylhexanoic acid and (S)-mandelic acid in water, an alcohol or a mixture of water and an alcohol; allowing a precipitate to form; introducing the precipitate into a polar aprotic solvent or a mixture of polar aprotic solvent and water to form a slurry; and collecting the solid from the slurry.

DETAILED DESCRIPTION OF THE INVENTION

In accordance with Scheme I below, the present invention provides an efficient synthesis of racemic isobutyl-GABA and a method for obtaining (S)-isobutyl-GABA from racemic isobutyl-GABA.

Scheme I

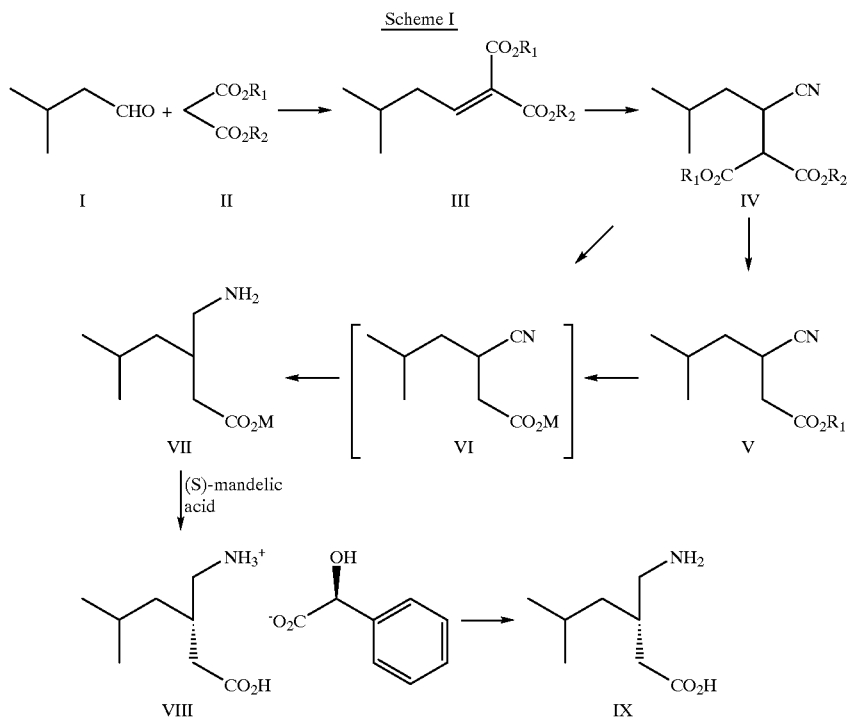

wherein $R_1$ and $R_2$ are the same or different and are hydrogen, $C_1$–$C_6$ alkyl, aryl, benzyl or $C_3$–$C_6$ cycloalkyl; and M is hydrogen, an alkali metal, or an alkaline earth metal.

Scheme I illustrates a method of making (±)-3-(aminomethyl)-5-methylhexanoic acid (VII or racemic 3-(aminomethyl)-5-methylhexanoic acid), the method comprising condensing isovaleraldehyde (I) with (II) to form (III); reacting (III) with a cyanide source to form (IV); decarboxylating (IV) to form (V); hydrolyzing (V) with an alkali metal or alkaline earth metal hydroxide to form (VI); and hydrogenating (VI) to form (±)-3-(aminomethyl)-5-methylhexanoic acid (VII).

In a preferred embodiment of the present method, (±)-3-(aminomethyl)-5-methylhexanoic acid can be made by condensing isovaleraldehyde (I) with (II) to form (III); reacting (III) with a cyanide source to form (IV); hydrolyzing and decarboxylating (IV) to form (VI); and hydrogenating (VI) to form (±)-3-(aminomethyl)-5-methylhexanoic acid (VII).

Also provided by the present invention is a method for obtaining (S)-3-(aminomethyl)-5-methylhexanoic acid (IX) from (±)-3-(aminomethyl)-5-methylhexanoic acid (VII), the method comprising combining (±)-3-(aminomethyl)-5-methylhexanoic acid and (S)-mandelic acid in water, an alcohol or a mixture of water and an alcohol; allowing a precipitate to form; introducing the precipitate into a polar aprotic solvent, or a polar aprotic solvent and water, to form a slurry; and collecting the solid from the slurry.

In one step of the present method for making (±)-3-(aminomethyl)-5-methylhexanoic acid, isovaleraldehyde is condensed with $$\begin{array}{c} CO_2R_1 \\ CO_2R_2 \end{array}$$

wherein $R_1$ and $R_2$ are the same or different and are hydrogen $C_1$–$C_6$ alkyl, aryl, benzyl, or $C_3$–$C_6$ cycloalkyl. This type of reaction is known to those skilled in the art as a Knoevenagel Condensation, and the conditions under which a Knoevenagel Condensation can be carried out are well known to those skilled in the art. For example, the condensation can be achieved using a catalytic amount of a base such as di-n-propylamine. Other suitable catalysts are known in the literature. See for example, Tietze L. F., and Beifuss U. in *Comprehensive Organic Synthesis,* 1991;2:341–394 (Trost B. M., ed.), Pergamon Press. Representative examples of suitable catalysts include pyrrolidine, β-alanine, ammonium acetate, di-isoproplyamine, and di-n-propylamine. These basic catalysts can also be used in combination with an acid such as p-toluene sulfonic acid or acetic acid. A preferred catalyst system in the present method is di-n-propylamine and acetic acid.

In general, the reaction is run in a refluxing hydrocarbon solvent including, but not limited to, toluene, hexane, heptane, methyl tert-butyl ether or cyclohexane, with the azeotropic removal of water. A preferred solvent is hexane. It is noted that olefin regioisomers can also be formed in the reaction, but are converted to the desired product in a subsequent step in the reaction sequence.

Representative examples of $C_1$–$C_6$ alkyl groups include methyl, ethyl, propyl, isopropyl, n-butyl, isobutyl, tert-butyl, pentyl and hexyl. Representative examples of $C_3$–$C_6$ cycloalkyl include cyclopropyl, cyclobutyl, cyclopentyl and cyclohexyl. Representative examples of aryl groups include phenyl and substituted phenyl, naphthyl, pridinyl, and the like. The aryl moiety may be substituted with one or more substituents, which can be the same or different. Examples of such groups include $C_1$–$C_6$ alkyl, $C_1$–$C_6$ alkoxy and halogen. Preferably, $R_1$ and $R_2$ are ethyl. In general, the isovaleraldehyde and

are added to the solvent along with the catalyst, and refluxed with azeotropic removal of water. It is also contemplated that additional catalyst may be added when the rate of azeotropic water collection slows. The progress of the condensation reaction may be monitored by methods well known in the art. A preferred monitoring method is gas chromatography (GC). In another step of the present method,

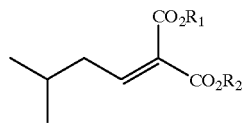

is reacted with a cyanide source to form

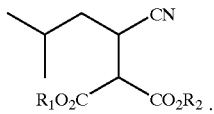

In general,

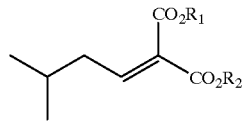

is reacted with a cyanide source in a polar protic solvent such as ethanol, methanol, n-propanol, isopropanol, a mixture of water and alcohols, or polar aprotic solvents such as dimethylsulfoxide (DMSO) or DMSO/water, and then treated with an acid. Examples of suitable cyanide sources include, but are not limited to, hydrogen cyanide, acetone cyanohydrin or an alkali metal or alkaline earth metal cyanide, such as sodium cyanide, potassium cyanide, or magnesium cyanide. The

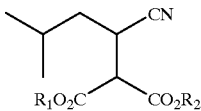

in this step may be used in the next step without purification, i.e. in crude form, or it may be purified. Examples of suitable acids are acetic acid, hydrochloric acid, hydrobromic acid, sulfuric acid, benzoic acid, mandelic acid, p-toluenesulfonic acid, and the like.

The

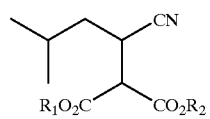

can be decarboxylated to form

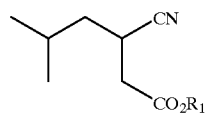

by heating

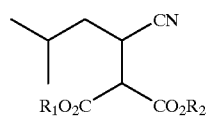

in a solvent with a salt. Examples of suitable solvents include mixtures of water and a polar solvent such as ethanol or dimethylsulfoxide (DMSO). Examples of suitable salts include alkali metal and alkaline earth metal halides such as sodium chloride and alkali metal and alkaline earth metal cyanides such as sodium cyanide, magnesium cyanide, and the like.

The

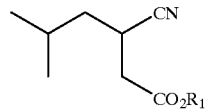

can be hydrolyzed with an alkali metal hydroxide or an alkaline earth metal hydroxide to form an alkali or alkaline earth metal carboxylate salt. The alkali or alkaline earth metal hydroxide can be any alkali or alkaline earth metal hydroxide known to those skilled in the art. Examples of suitable alkali metal hydroxides include sodium hydroxide, lithium hydroxide, and potassium hydroxide. Examples of suitable alkaline earth metal hydroxides include calcium hydroxide and magnesium hydroxide. The reaction is usually run in a suitable protic solvent such as water or a mixture of water and a polar protic solvent such as methanol, ethanol, or isopropanol.

The carboxylate salt can be reduced to give the alkali or alkaline earth metal salt of (±)-3-(aminomethyl)-5-methylhexanoic acid. The carboxylate salt can be protonated with mineral acids or carboxylic acids to give the carboxylic acid and then the nitrile group of the carboxylic acid can be reduced. Conversely, the nitrile group of the carboxylate salt can be reduced, and subsequently protonated to form the carboxylic acid. The salt can be treated with mineral acids or carboxylic acids to give (±)-3-(aminomethyl)-5-methylhexanoic acid. Those skilled in the art are familiar with the reduction of nitrile functional groups. One common method of reducing a nitrile uses a hydrogenation catalyst, such as sponge nickel, in the presence of hydrogen. Other catalysts include palladium, platinum, rhodium, cobalt, and nickel. In general, the reaction is run in a solvent system such as a mixture of water and a polar protic solvent.

The amino carboxylate formed after nitrile reduction can be obtained in the acid form by treating the amino carboxylate with an acid. The mineral acids such as hydrochloric acid can be used. Carboxylic acids, such as acetic acid, can also be used. Preferably, the acid is acetic acid, as a byproduct formed by the reaction is MOAc where M is an alkali metal ion (Na, K, and the like), and OAc is an acetate ion. The salt MOAc is more soluble in aqueous alcoholic solvents than inorganic salts such as sodium chloride, potassium chloride, and the like. Thus, isolation of the product is simplified, and the need for ion exchange treatment to remove excess salts is avoided.

The cyano acid may also be reduced using a suitable hydrogenation catalyst, such as sponge nickel and hydrogen, in a polar solvent such as methanol, ethanol, or isopropanol in combination with ammonia or a mixture of ammonia and water. Examples of other suitable hydrogenation catalysts include palladium, platinum, rhodium, cobalt, and nickel.

In a preferred method

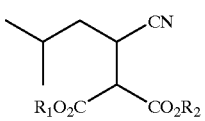

is taken to (±)-3-(aminomethyl)-5-methylhexanoic acid without isolation of intermediates. For example,

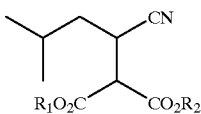

can be hydrolyzed using an alkali or alkaline earth metal hydroxide such as potassium hydroxide or sodium hydroxide in an alcohol solvent, which promotes decarboxylation. Further hydrolysis using an alkali or alkaline earth metal hydroxide in water, an alcohol, or a mixture of water and an alcohol, gives carboxylate (VI), which can be reduced with a hydrogenation catalyst followed by treatment with a mineral acid to give racemic 3-(aminomethyl)-5-methylhexanoic acid.

Racemic 3-(aminomethyl)-5-methylhexanoic acid can be resolved, i.e., the enantiomers separated, by selective crystallization with (S)-mandelic acid. Racemic 3-(aminomethyl)-5-methylhexanoic acid and (S)-mandelic acid can be combined in a solvent such as water or an alcohol or a mixture of water and an alcohol to form a salt. Examples of suitable alcohols include methanol, ethanol, n-propanol, isopropanol, n-butanol, tert-butanol, and the like. In general, the S,S salt precipitates from the solution, and the diastereomer, the R,S salt, stays in solution. Diasteriomeric purity of the S,S salt can be enhanced by further crystallizations. Additional (S)-mandelic acid can be included in the recrystallizations to enhance diastereomeric enrichment. In general, an excess of mandelic acid is used. It is also noted that mandelic acid can be used in combination with another acid in accordance with the "Pope-Peachy" method known in the art.

Removal of (S)-mandelic acid from the salt to give enriched (S)-3-(aminomethyl)-5-methylhexanoic acid can be done using a polar aprotic solvent such as dimethylsulfoxide or mixtures of dimethylsulfoxide and water or tetrahydrofuran and water, at temperatures typically in the range of about 0° C. to about 100° C.

Trituration to obtain the S-enantiomer has the advantage that it is operationally simple and more economical than traditional acid/base or ion exchange methods.

Alternatively, (S)-3-(aminomethyl)-5-methylhexanoic acid can be obtained by combining (±)- 3-(aminomethyl)-5-methylhexanoic acid with (R)-mandelic acid to give the R,R salt which crystallizes out of the solution leaving the solution enriched in (S)-3-(aminomethyl)-5-methylhexanoic acid which can then be isolated from the solution by methods well known to those skilled in the art.

The (R)-mandelic salt of (S)-3-(aminomethyl)-5-methylhexanoic acid can be isolated as an intermediate, treated with a polar aprotic solvent or mixture of water and a polar aprotic solvent to give the (S)-3-(aminomethyl)-5-methylhexanoic acid.

It is also possible to obtain (S)-3-(amino methyl)-5-methylhexanoic acid from racemic isobutyl-GABA by standard methods of resolution known to those skilled in the art. It is noted that the isolated solids may be dried at each stage in the resolution or carried on to the next step as solvent-wet solids with comparable results.

Also provided by the present invention are the novel compounds

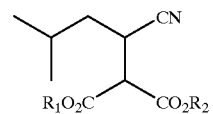

where $R_1$ and $R_2$ are the same or different and are hydrogen, $C_1$–$C_6$ alkyl, aryl, benzyl or $C_3$–$C_6$ cycloalkyl;

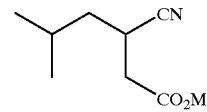

where M is hydrogen, an alkali metal, or an alkaline earth metal;

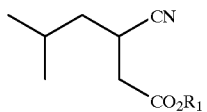

where $R_1$ is a defined above; and

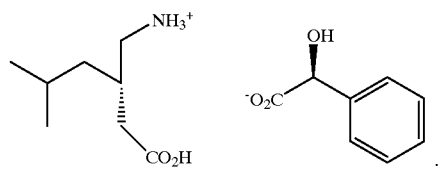

It is also contemplated that the compounds of the present method can be found or isolated in the form of hydrates or solvates, which are considered to fall within the scope of the present invention.

The examples below are intended to illustrate specific embodiments of the invention and are not intended to limit the scope of the specification, including the claims, in any manner.

EXAMPLES

Preparation of 2-Carboxyethyl-5-methylhex-2-enoic acid, ethyl ester

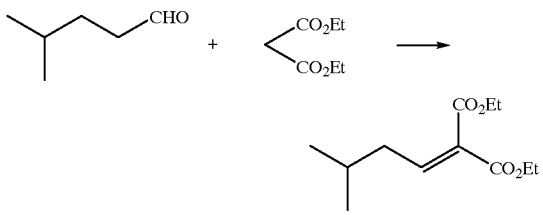

Isovaleraldehyde (361.6 kg, 4198.3 mol) was combined with diethyl malonate (640.8 kg, 4000.7 mol), hexane (1000 L), di-n-propylamine (20.0 kg, 197.6 mol), and glacial acetic acid (24.0 kg, 399.7 mol) in a 4000 L vessel. The mixture was heated to reflux (jacket temperature set at 90° C.) with continuous removal of water until the rate of water collection slowed significantly (69.4 kg water was collected versus 72.0 kg expected by theory).

At this point, the mixture was cooled to below 60° C. and a second catalyst addition was carried out by charging di-n-propylamine (20.0 kg, 197.6 mol), and glacial acetic acid (24.0 kg, 399.7 mol) to the mixture. (The second catalyst addition is optional, but helps to bring the reaction to completion faster. This modification shows improved purity profiles and yields in some cases versus a single catalyst charge.)

The mixture was heated to reflux (jacket temperature set at 90° C.) with continuous removal of water for an additional 22.5 hours or until the reaction is judged complete by GC assay (>90% combined product and isomer). The mixture was brought to <40° C. and was washed with water (2×800 L). The organic layer was concentrated by atmospheric pressure distillation until most of the hexane was removed. The remaining oil was further concentrated by vacuum distillation at 40° C. for 2–18 hours.

The product was obtained as a colorless liquid (810.0 kg, 88.7% yield) and contained a mixture of olefin isomers (both of which are converted to the same product in the next synthetic step). The major isomer is 2-carboxyethyl-5-methylhex-2-enoic acid, ethyl ester; the minor isomer (typically 10–13% by GC) is believed to be 2-carboxyethyl-5-methylhex-3-enoic acid, ethyl ester.

Description: Colorless to yellow liquid

GC Assay: 74–76% 2-carboxyethyl-5-methylhex-2-enoic acid ethyl ester; 10–13% 2-carboxyethyl-5-methylhex-3-enoic acid ethyl ester; 87–88% Total of both isomers.

$^1$H NMR, Note: Chemical shifts and multiplicities are reported as observed for a sample of the mixture prepared by the process described above. The observed integration results are slightly different than would be expected for pure 2-carboxyethyl-5-methylhex-2-enoic acid ethyl ester due to the presence of two olefin isomers. Thus, the integration has been reported as would be expected for a pure sample of 2-carboxyethyl-5-methylhex-2-enoic acid ethyl ester.

$^1$H NMR (CDCl$_3$, 200 MHz): δ 0.91–1.02 (m, 6H), 1.23–1.37 (m, 6H), 1.78–1.85 (m, 1H), 2.16–2.23 (m, 2H) 4.19–4.36 (m, 4H), 7.02 (t, 1H, J=7.9 Hz).

Boiling Point: Purified samples can be obtained by vacuum distillation: 101–104° C. at 1.1–1.2 mm Hg; or 132° C. at 5 mm Hg.

Preparation of 2-Carboxyethyl-3-cyano-5-methylhexanoic acid, ethyl ester

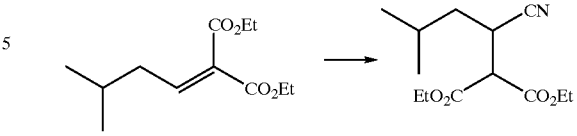

2-Carboxyethyl-5-methylhex-2-enoic acid ethyl ester (692.7 kg, 3034 mol) was charged to a 4000 L vessel containing potassium cyanide (172.6 kg, 2650 mol) and 2B ethanol (700 kg). The resulting slurry was stirred at 25–40° C. for at least 18 hours or until in-process HPLC assay indicated less than 5% 2-carboxyethyl-5-methylhex-2-enoic acid, ethyl ester (typically 22–24 hours). Hexane (890 L) was charged to the slurry. Glacial acetic acid (175 kg, 2914 mol) was slowly added keeping the temperature <35° C. To the resulting thick slurry was added water (820 L) with stirring. The layers were separated. The aqueous layer was extracted with hexane (1×890 L). The organic layers were combined and washed with water (1×420 L). The water layer was separated and the remaining organic solution was distilled at atmospheric pressure until most of the hexane was removed. The oil was then further concentrated by vacuum distillation at 40° C. for 2–19 hours. The product was obtained as a liquid (752.6 kg, 93.8%).

Description: Colorless to orange liquid

HPLC Assay: 83–86% 2-carboxyethyl-3-cyano-5-methylhexanoic acid, ethyl ester $^1$H NMR (DMSO-d$_6$, 200 MHz): δ 0.92 (t, 6H, J=6.1 Hz), 1.15–1.21 (m, 6H), 1.23–1.36 (m, 1H), 1.54–1.68 (m, 2H), 3.25–3.33 (m, 1H), 3.97 (d, 1H, J=6.5 Hz), 4.10–4.25 (m, 4H).

Preparation of 3-Cyano-5-methylhexanoic acid, ethyl ester

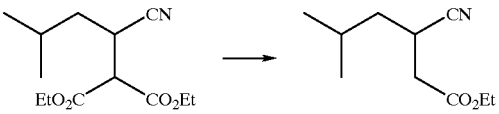

An 800 L still was charged with sodium chloride (21 kg, 359 mol), 2-carboxyethyl-3-cyano-5-methylhexanoic acid, ethyl ester (80.0 kg, 313 mol), dimethylsulfoxide (238 kg), and water (10.8 kg, 600 mol). The mixture was heated to 137–148° C. for 8.5 hours. The mixture was cooled to below 50° C., and treated with methyl tert-butyl ether (125 kg). The mixture was cooled to 0–10° C., and treated with water (160 L) in portions to maintain the temperature below 40° C. After stirring for 15–30 minutes, the phases were separated. The aqueous phase was extracted with methyl tert-butyl ether (125 kg). The organic extracts were combined with a vessel rinse (25 kg methyl tert-butyl ether) and was extracted with water (110 L). The water phase was discarded. The methyl tert-butyl ether phase was concentrated by atmospheric pressure distillation to a batch temperature of about 65° C. The batch was cooled to 30–40° C. and further concentrated by vacuum distillation until the solvent content was acceptable (<5% methyl tert-butyl ether by area % GC analysis). The product was obtained as a brown oil (51.3 kg, 85.7%).

Description: Colorless to dark brown oil

GC Assay (area %): 86.20%

Boiling Point: Purified samples can be obtained by vacuum distillation: 99–103° C. at 1.3–1.5 mm Hg $^1$H NMR (CDCl$_3$, 200 MHz): δ 0.88–0.99 (m, 6H), 1.19–1.40 (m, 4H), 1.57–1.69 (m, 1H), 1.72–1.84 (m, 1H), 2.53 (dd, 1H, J=6.8 Hz, J=16.6 Hz), 2.70 (dd, 1H, J=7.4 Hz, J=16.5 Hz), 2.99–3.10 (m, 1H), 4.21 (q, 2H, J=7.1 Hz).

Preparation of Racemic 3-(Aminomethyl)-5-methylhexanoic acid

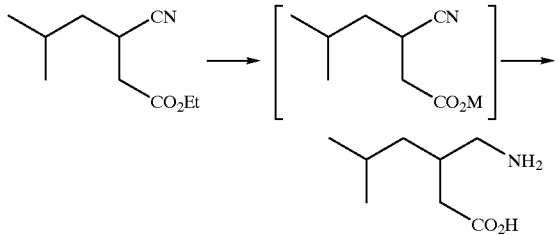

An 800 L still was charged with 3-cyano-5-methyl hexanoic acid, ethyl ester (50.1 kg, 273 mol) and ethyl alcohol 2B (53 kg). A solution of potassium hydroxide (17.8 kg, 317 mol) in water (56 L) was added controlling the addition rate to maintain the batch temperature below 25° C. The mixture was stirred at 20–25° C. for about 1.5 hours.

The batch was transferred to a hydrogenator containing sponge nickel (15.0 kg, 50% water wet), followed by a rinse of ethyl alcohol 2B (27 kg). The mixture was treated with hydrogen at about 50 psi for about 19 hours (hydrogen uptake stopped).

The nickel was removed by filtration and the filter cake was rinsed with a mixture of 39 kg ethyl alcohol 2B and 111 L water. To the filtrate was added glacial acetic acid (22.8 kg, 380 mol) maintaining the batch temperature less than 40° C. The batch was heated to 70–75° C. to dissolve the solids. The batch was slowly cooled to 0–5° C. to crystallize the product.

The solid was collected on a centrifuge and rinsed with 160 L isopropyl alcohol that was previously cooled to 0–5° C.

The damp solid was dried in a vacuum tray drier under vacuum at 35–45° C. (28 hours) to give 31.4 kg (75.1%) of racemic 3-aminomethyl-5-methylhexanoic acid.

The product was characterized by HPLC and NMR. The water content for this product was 9.51% by weight (Karl Fischer). The product may contain a variable amount of water ranging from nearly anhydrous up to about 10.2% (monohydrate).

Description: White to off-white solid
HPLC Assay: 102.05% w/w
Melting Point: 166.0–167.5° C.
$^1$H NMR (D$_2$O, 200 MHz): δ 0.86–0.90 (m, 6H), 1.21 (t, 2H, J=7.0 Hz), 1.62–1.69 (m, 1H), 2.12–2.35 (m, 3H), 2.94–3.00 (m, 2H).

Preparation of Racemic 3-(Aminomethyl)-5-methylhexanoic acid

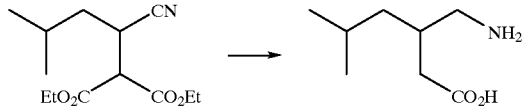

A 2000 L still was charged with 2-carboxyethyl-3-cyano-5-methyl hexanoic acid, ethyl ester (286 kg, 1120 mol) and methyl alcohol (100 L). A solution of potassium hydroxide (60.8 kg, 1046 mol) in methyl alcohol (260 L) was added controlling the addition rate so as to keep the batch temperature about 20–35° C. A rinse of 40 L methyl alcohol was added to the batch and the mixture was heated to reflux for 4–5 hours. The batch was cooled to 25–30° C. and a solution of potassium hydroxide (121.6 kg, 2167 mol) in water (200 L) was added maintaining the batch temperature below 50° C.

The batch was concentrated by vacuum distillation to about 580 L volume. Water (100 L) was added and the distillation continued to a volume of about 510 L.

The batch was transferred to an 800 L hydrogenator containing 44.8 kg sponge nickel (50% water wet), along with a mixture of 20 L water and 30 kg ethyl alcohol 2B as a rinse. The mixture was treated with hydrogen at about 50 psi for about 18–19 hours (hydrogen uptake stopped).

To the batch was added 58 kg ethyl alcohol 2B and the nickel was removed by filtration. The filter cake was rinsed with a mixture of 100 kg ethyl alcohol 2B and 270 L water.

The filtrate was transferred to a 2000 L still containing 222 kg (3697 mol) glacial acetic acid at 50–60° C. controlling the addition rate to control gas evolution and to maintain the temperature at 50–60° C. A rinse of 40 L water was added to the batch and the temperature increased to 70–75° C. to dissolve the solids. The batch was slowly cooled to 0–5° C. to crystallize the product.

The solid was collected on a centrifuge and rinsed with 570 L isopropyl alcohol.

The damp solid was dried in a vacuum tray drier under vacuum at 35–45° C. (22 hours) to give 108.1 kg (72.7%) of racemic 3-aminomethyl-5-methylhexanoic acid. The product was characterized by HPLC and NMR. The product may contain variable amounts of water ranging from nearly anhydrous (1.68% by weight in this example) up to about 10.2% (monohydrate).

Description: White to off-white solid
HPLC Assay: 99.67% w/w
Melting Point: 166.0–167.5° C.
$^1$H NMR (D$_2$O, 200 MHz): δ 0.88–0.92 (m, 6H), 1.23 (t, 2H, J=6.9 Hz), 1.64–1.70 (m, 1H), 2.13–2.37 (m, 3H), 2.96–3.01 (m, 2H).

Resolution of Racemic 3-(Aminomethyl)-5-methylhexanoic acid

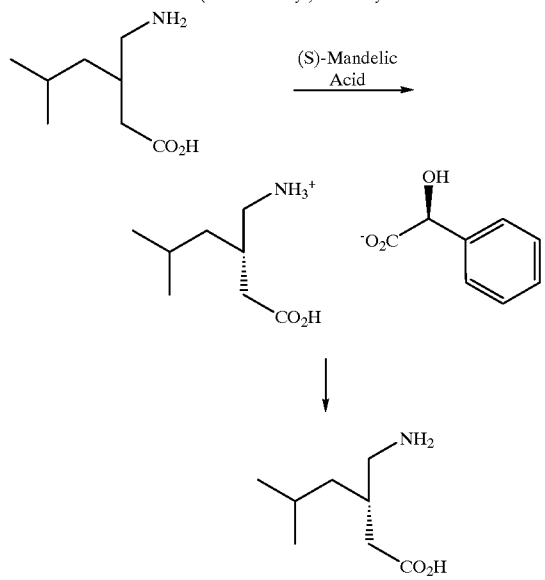

A solution of 3% v/v water in isopropyl alcohol was prepared by mixing water (9 kg) and isopropyl alcohol (291

L) in a 400 L reactor. This was repeated. The solvent was stored in plastic drums and used as necessary (described below).

A 400 L still was charged with racemic 3-aminomethyl-5-methylhexanoic acid (29.7 kg, 168 mol), S-(+)-mandelic acid (39.3 kg, 258 mol), and 3% v/v water/isopropyl alcohol solution (244 kg) prepared earlier. The mixture was heated to dissolve the solids (about 65–80° C.), cooled, and seeded with S,S-salt to crystallize the mixture of diastereomeric mandelate salts enriched in the S,S-isomer. The solid was collected on a centrifuge and rinsed with 3% water/isopropanol (21.5 kg). (S/R isomer ratio: 93.7% S: 6.3% R. The solid may optionally be dried at this stage or carried on as a solvent-wet solid).

The damp salt was charged to a 400 L still along with (S)-(+)-mandelic acid (5.8 kg, 38 mol) and 3% water/isopropyl alcohol (121 kg). The mixture was heated to dissolve the solids (about 65–80° C.), cooled, and seeded if necessary, with S,S-salt to crystallize the mixture of diastereomeric mandelate salts further enriched in the S,S-isomer. The solid was collected on a centrifuge and rinsed with 3% water/isopropyl alcohol (33.3 kg). The solid may optionally be dried at this stage or carried on as a solvent-wet solid (S/R isomer ratio: 99.5% S:0.5% R). The dried S,S-salt typically has the following characteristics: Description: White to off-white solid; mp 133–134° C.;

$^1$H NMR (D$_2$O, 200 MHz): δ 0.87–0.92 (m, 6H), 1.24 (t, J=7.2 Hz, 2H), 1.55–1.76 (m, 1H), 2.11–2.52 (m, 3H), 3.00 (d, J=6.2 Hz, 2H), 5.07 (s, 1H), 7.43 (s, 5H).

The damp salt was transferred to a 400 L reactor with tetrahydrofuran (195 L) and water (10 kg). The mixture was warmed to 60–65° C., and cooled to 0–5° C. The crude (S)-isobutyl GABA solid was collected on a centrifuge and rinsed with a mixture of tetrahydrofuran (28 L)/water (1 kg). The solid may optionally be dried at this stage or carried on as a solvent-wet solid (S/R isomer ratio: 100% S:<0.05% R isomer (not detected)).

The damp solid was transferred to a 200 L still with isopropyl alcohol (113 L) and water (38 kg). The mixture was heated to dissolve the solids (about 75–80° C.), filtered while hot, and cooled to 0–5° C. to crystallize the (S)-isobutyl GABA. The solid was collected on a centrifuge and rinsed with 25 L isopropyl alcohol. The damp solid was dried in a vacuum tray drier under vacuum at 35–45° C. to give 7.4 kg (S)-isobutyl GABA.

Description: White to off-white solid

HPLC Assay: 99.4% w/w

Chiral Purity (HPLC): 100% S; R-isomer not detected (limit of detection 0.05%)

Melting Point: 177–179° C. (decomposes)

$^1$H NMR (D$_2$O, 200 MHz): δ 0.88–0.92 (m, 6H), 1.23 (t, 2H, J=6.9 Hz), 1.64–1.70 (m, 1H), 2.13–2.32 (m, 3H), 2.96–3.01 (m, 2H).

Resolution of Racemic 3-(Aminomethyl)-5-Methylhexanoic Acid

A solution of 3% v/v water in isopropyl alcohol was prepared by mixing water (5.7 kg) and isopropyl alcohol (184 L) in a 400 L reactor. The solvent was stored in plastic drums and used as necessary (described below).

A 2000 L reactor was charged with racemic 3-aminomethyl-5-methylhexanoic acid (117.6 kg, 673 mol). A 2000 L still was charged with water (36 L), S-(+)-mandelic acid (153.0 kg, 1006 mol), and isopropyl alcohol (1170 L). The mandelic acid mixture was heated to 55–65° C. and the resulting solution was transferred to the reactor containing racemic 3-aminomethyl-5-methylhexanoic acid. The batch was heated to 50–65° C. just long enough to dissolve the solids.

[Note: Batch heating and temperature are kept to the minimum necessary to dissolve solids in order to minimize acid catalyzed decomposition of racemic 3-aminomethyl-5-methylhexanoic acid to the corresponding lactam. This decomposition is undesired because it lowers product yield.]

The mixture was cooled to 40–45° C., seeded with S,S-salt (20 g), and further cooled to 20–25° C. to crystallize the mixture of diastereomeric mandelate salts enriched in the S,S-isomer. After maintaining the temperature at 20–25° C. for at least 12 hours, the solid was collected on a centrifuge and rinsed with 3% water/isopropanol solution (100 kg) prepared earlier.

[Note: S/R isomer ratio: 92.5% S:7.5% R. The solid may optionally be dried at this stage or carried on as a solvent-wet solid.]

The solvent-wet S,S-salt was charged to an 800 L reactor. An 800 L still was charged with water (14.4 kg), (S)-(+)-mandelic acid (23.0 kg, 151 mol), and isopropyl alcohol (468 L). The mandelic acid mixture was heated to 65–70° C., and the resulting solution was transferred to the reactor containing the solvent-wet salt. The batch was heated to 60–70° C. just long enough to dissolve the solids or, if solids do not dissolve, until batch temperature reached 70° C.

[Note: Batch heating and temperature are kept to the minimum necessary either to dissolve solids or to reach 70° C., in order to minimize acid catalyzed decomposition to the corresponding lactam. This decomposition is undesired because it lowers product yield.]

The mixture was cooled to 50–55° C. Seeding with S,S-salt at this temperature range is optional but is typically not needed to induce crystallization or further diastereomeric enrichment. The batch was further cooled to 0–5° C. to crystallize the mixture of diastereomeric mandelate salts enriched in the S,S-isomer. After maintaining the temperature at 0–5° C. for at least 12 hours, the solid was collected on a centrifuge and rinsed with 3% water/isopropanol solution (100 kg) prepared earlier.

[Note: S/R isomer ratio: 98.6% S:1.4% R. The solid may optionally be dried at this stage or carried on as a solvent-wet solid. The dried S,S-salt typically has the following characteristics:

Description: White to off-white solid; mp 133–134° C. [36832×88];

$^1$H NMR (D$_2$O, 200 MHz): δ 0.87–0.92 (m, 6H), 1.24 (t, J=7.2 Hz, 2H), 1.55–1.76 (m, 1H), 2.11–2.52 (m, 3H), 3.00 (d, J=6.2 Hz, 2H), 5.07 (s, 1H), 7.43 (s, 5H).]

An 800 L reactor was charged with water (31 L), the solvent-wet S,S-salt, and tetrahydrofuran (595 L). The mixture was warmed to 50–55° C., and cooled to 0–5° C. After maintaining the temperature at 0–5° C. for at least 12 hours, the solid was collected on a centrifuge and rinsed with tetrahydrofuran (50 L) and then with isopropyl alcohol (50 L).

[Note: S/R isomer ratio: 99.94% S:0.06% R. The solid may optionally be dried at this stage or carried on as a solvent-wet solid.]

An 800 L reactor was charged with water (155 L), the solvent-wet CI-1008, and isopropyl alcohol (465 L). The mixture was heated to dissolve the solids (about 75–80° C.), filtered while hot, cooled to 40–45° C., seeded with CI-1008 (10 g), and further cooled to 0° C. to –5° C. to crystallize the CI-1008. The solid was collected on a centrifuge and rinsed with isopropyl alcohol (50 L). The damp solid was dried in a vacuum tray drier under vacuum at 35–45° C. to give 32.4 kg CI-1008 (60.4% yield).

Description: White to off-white solid

HPLC Assay: 100.32% w/w

Chiral Purity (HPLC): 100% S; R-isomer not detected (limit of detection 0.05%)

1H NMR (D$_2$O, 200 MHz): δ 0.86–0.90 (m, 6H), 1.21 (t, 2H, J=7.1 Hz), 1.62–1.65 (m, 1H), 2.15–2.35 (m, 3H), 2.94–2.99 (m, 2H). [CD 2586]

Melting Point: 177–179° C. (decomposes)

We claim:

1. The compound having the formula

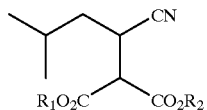

wherein $R_1$ and $R_2$ are the same or different and are hydrogen, $C_1$–$C_6$ alkyl, aryl, benzyl or $C_3$–$C_6$ cycloalkyl.

2. The compound of claim 1 wherein $R_1$ and $R_2$ are ethyl.

* * * * *